US008764836B2

(12) United States Patent
De Wilde et al.

(10) Patent No.: US 8,764,836 B2
(45) Date of Patent: Jul. 1, 2014

(54) CIRCULAR GLENOID METHOD FOR SHOULDER ARTHROPLASTY

(76) Inventors: Lieven De Wilde, Ghent (BE); Kyle Lappin, Ft Wayne, IN (US)

(*) Notice: Subject to any disclaimer, the term of this patent is extended or adjusted under 35 U.S.C. 154(b) by 0 days.

(21) Appl. No.: 13/051,011

(22) Filed: Mar. 18, 2011

(65) Prior Publication Data

US 2012/0239155 A1 Sep. 20, 2012

(51) Int. Cl.
*A61F 2/40* (2006.01)
(52) U.S. Cl.
USPC .................................... 623/19.11; 623/908
(58) Field of Classification Search
USPC ................... 623/19.11–19.14, 902, 908
See application file for complete search history.

(56) References Cited

U.S. PATENT DOCUMENTS

| 2,487,203 | A | 11/1949 | Wilber |
| 3,855,638 | A | 12/1974 | Pilliar |
| 4,030,143 | A | 6/1977 | Elloy et al. |
| 4,964,865 | A | 10/1990 | Burkhead et al. |
| 5,030,219 | A | 7/1991 | Matsen, III et al. |
| 5,080,673 | A | 1/1992 | Burkhead et al. |
| 5,180,384 | A | 1/1993 | Mikhail |
| 5,324,295 | A | 6/1994 | Shapiro |
| 5,489,310 | A | 2/1996 | Mikhail |
| 5,800,551 | A | 9/1998 | Williamson et al. |
| 5,919,195 | A | 7/1999 | Wilson et al. |
| 6,045,302 | A | 4/2000 | Orr |
| 6,228,900 | B1 | 5/2001 | Shen et al. |
| 6,245,074 | B1 | 6/2001 | Allard et al. |
| 6,281,264 | B1 | 8/2001 | Salovey et al. |
| 6,364,910 | B1 | 4/2002 | Shultz et al. |
| 6,379,386 | B1 | 4/2002 | Resch et al. |
| 6,679,916 | B1 | 1/2004 | Frankle et al. |
| 6,699,289 | B2 | 3/2004 | Iannotti et al. |
| 6,783,549 | B1 | 8/2004 | Stone et al. |
| 7,294,133 | B2 | 11/2007 | Zink et al. |
| 7,329,284 | B2 | 2/2008 | Maroney et al. |
| 7,338,498 | B2 | 3/2008 | Long et al. |
| 7,604,665 | B2 | 10/2009 | Iannotti et al. |
| 2003/0125809 | A1 | 7/2003 | Iannotti et al. |
| 2004/0097947 | A1 | 5/2004 | Wolford et al. |
| 2004/0193168 | A1 | 9/2004 | Long et al. |
| 2005/0278030 | A1 | 12/2005 | Tornier et al. |
| 2006/0015112 | A1 | 1/2006 | McGovern |
| 2006/0020344 | A1* | 1/2006 | Shultz et al. ............... 623/19.12 |

(Continued)

FOREIGN PATENT DOCUMENTS

| CH | 693446 A5 | 8/2003 |
| GB | 2406278 A | 3/2005 |
| WO | 2011005205 A1 | 1/2011 |

OTHER PUBLICATIONS

Math Open Reference Website: 'Circle in Three Points', Accessed Oct. 12, 2012.*

(Continued)

*Primary Examiner* — Marcia Hoffman
(74) *Attorney, Agent, or Firm* — Maginot, Moore & Beck LLP (57) ABSTRACT

A method of shoulder arthroplasty in one embodiment includes accessing a scapula, identifying an inferior glenoid circle center of the scapula, preparing a glenoid fossa of the scapula to receive a prosthesis, selecting a glenoid component, and implanting the selected glenoid component based upon the identified inferior glenoid circle center in the prepared glenoid fossa.

20 Claims, 6 Drawing Sheets

(56) References Cited

U.S. PATENT DOCUMENTS

| | | | |
|---|---|---|---|
| 2006/0069444 A1 | 3/2006 | Deffenbaugh | |
| 2006/0111787 A1 | 5/2006 | Bailie et al. | |
| 2006/0195194 A1 | 8/2006 | Gunther | |
| 2007/0016304 A1* | 1/2007 | Chudik | 623/19.11 |
| 2007/0055249 A1 | 3/2007 | Jensen et al. | |
| 2007/0251356 A1 | 11/2007 | Tribby | |
| 2007/0260321 A1 | 11/2007 | Stchur | |
| 2010/0070044 A1 | 3/2010 | Maroney et al. | |
| 2010/0087876 A1 | 4/2010 | Gunther | |
| 2010/0161065 A1 | 6/2010 | Williams, Jr. et al. | |
| 2010/0274359 A1 | 10/2010 | Brunnarius et al. | |
| 2011/0028977 A1 | 2/2011 | Rauscher et al. | |
| 2012/0130499 A1 | 5/2012 | Long | |

OTHER PUBLICATIONS

Bey, Michael J., et al., "Measuring Dynamic In-Vivo Glenohumeral Joint Kinematics: Technique and Preliminary Results," Journal of Biomechanics 41 (2008), pp. 711-714. (4 pages).

Chant, Chris B., et al., "Humeral Head Retroversion in Competitive Baseball Players and Its Relationship to Glenohumeral Rotation Range of Motion," Journal of Orthopaedic & Sports Physical Therapy, Sep. 2007, vol. 37, No. 9, pp. 514-520. (7 pages).

Conzen, Annemarie and Eckstein, Felix, MD, "Quantitative Determination of Articular Pressure in the Human Shoulder Joint," Journal of Shoulder and Elbow Surgery, vol. 9, No. 3, May/Jun. 2000, pp. 196-204. (9 pages).

De Wilde, Lieven F. MD, et al., "Glenohumeral Relationship in the Transverse Plane of the Body," Journal of Shoulder and Elbow Surgery, vol. 12, No. 3, May/Jun. 2003, pp. 260-267. (8 pages).

De Wilde, L.F., et al., "About the Variability of the Shape of the Glenoid Cavity," Surgical and Radiologic Anatomy (2004) 26; pp. 54-59. (6 pages).

Fleiss, Joseph L., "Analysis of Data From Multiclinic Trials," Controlled Clinical Trials 7: 267-275 (1986). (9 pages).

Hertel, Ralph M.D., "Geometry of the Proximal Humerus and Implications for Prosthetic Design," Journal of Shoulder and Elbow Surgery, Jul./Aug. 2002, vol. 11, No. 4, pp. 331-338. (8 pages).

Mansat, M. and Fourcade, D., "Preoperative Planning in Shoulder Prosthesis," Acta Orthopaedica Belgica (1995) vol. 61—Suppl. Jan. 1995. (6 pages).

Middernacht, Bart, MD, et al., "Consequences of Scapular Anatomy for Reversed Total Shoulder Arthroplasty,"Clinical Orthopaedics and Related Research (2008) 466: 1410-1418. (9 pages).

Moon, P. and Spencer, D.E., Rectangular Coordinates (x,y,z). Field Theory Handbook, Including Coordinate Systems, Differential Equations, and Their Solutions (1988), New York: Springer-Verlag, pp. 9-11 (Table 1.01). (3 pages).

Pearl, Michael L., M.D. and Volk, Albert G., M.D., "Coronal Plane Geometry of the Proximal Humerus Relevant to Prosthetic Arthroplasty, Journal of Shoulder and Elbow Surgery," vol. 5, No. 4, Jul./Aug. 1996, pp. 320-326. (7 pages).

Pearl, ML and Volk, AG, "Retroversion of the Proximal Humerus in Relationship to Prosthetic Replacement Arthroplasty," Journal of Shoulder and Elbow Surgery, Jul. 1995, vol. 4, No. 4, pp. 286-289. (4 pages).

Randelli, M., M.D. and Gambrioli, P.L., M.D., "Glenohumeral Osteometry by Computed Tomography in Normal and Unstable Shoulders," Clinical Orthopaedics and Related Research, No. 208, Jul. 1986, pp. 151-156. (6 pages).

Robertson, Douglas D., M.D., et al., " Three-Dimensional Analysis of the Proximal Part of the Humerus: Relevance to Arthroplasty," The Journal of Bone and Joint Surgery, vol. 82-A,No. 11, Nov. 2000, pp. 1594-1602. (9 pages).

Rougraff, Bruce T., M.D., et al., "Does Length of Symptoms Before Diagnosis of Sarcoma Affect Patient Survival?" Clinical Orthopaedics and Related Research (2007), No. 462, pp. 181-189. (9 pages).

Shrout, Patrick E. and Fleiss, Jospeh L., "Intraclass Correlations: Uses in Assessing Rater Reliability," Psychological Bulletin, 1979, vol. 86, No. 2, pp. 420-428. (9 pages).

Soslowsky, Louis J., Ph.D. et al, "Articular Geometry of the Glenohumeral Joint," Clinical Orthopaedics and Related Research, No. 285, Dec. 1992, pp. 181-190. (10 pages).

Tetreault, Patrice, et al., "Glenoid Version and Rotator Cuff Tears," Journal of Orthopaedic Research 22 (2004) pp. 202-207. (6 pages).

Warner, Jon J.P., M.D. et al, "Articular Contact Patterns of the Normal Glenohumeral Joint," Journal of Shoulder and Elbow Surgery, Jul./Aug. 1998, vol. 7, No. 4, pp. 381-388. (8 pages).

Westerhoff, P., et al., "In Vivo Measurement of Shoulder Joint Loads During Activities of Daily Living," Journal of Biomechanics 42 (2009), pp. 1840-1849. (10 pages).

Williams, Gerald R., Jr., M.D., and Iannotti, Joseph P., M.D. PhD., "Options for Glenoid Bone Loss: Composites of Prosthetics and Biologics," Journal of Shoulder and Elbow Surgery, Sep./Oct. 2007, vol. 16, No. 5S, pp. 267S-272S. (6 pages).

Wirth, Michael A., M.D. and Rockwood, Charles A., Jr., M.D., "Complications of Shoulder Arthroplasty," Clinical Orthopaedics and Related Research, Oct. 1994, No. 307, pp. 47-69. (23 pages).

Jeske, H.C. et al., "Normal glenoid rim anatomy and the reliability of shoulder instability measurements based on intrasite correlation," Surg. Radiol. Anat., vol. 31, pp. 623-625, Mar. 2009 (3 pages).

Erichsen, "Injuries of the Nervous System on Railway and Other Injuries of the Nervous System", The Classic Article in Clinical Orthoedics and Related Research, Mar. 1997, pp. 47-51, No. 458, Walton and Moberly, London (5 pages).

Iannotti JP, Gabriel JP, Schneck SL, Evans BG, Misra S., "The normal glenohumeral relationships. An anatomical study of one hundred and forty shoulder." J. Bone Joint Surg Am. 1992;74(4); 491-500. No doi found. (11 pages).

Karduna AR, Williams GR, Williams JL, Ianotti JP., "Glenohumeral Joint translations before and after total shoulder arthroplasty." J Bone Joint Surg 1997;79-A,1166-74. No doi found. (10 pages).

Lee SB, Kim KJ, O'Driscoll SW, Morrey BF, An KN., "Dynamic glenohumeral stability provided by the rotator cuff muscles in the mid-range and end-range of motion." A study in cadavera. J. Bone Joint Surg Am. 2000;82(6):849-57. No doi found (10 pages).

Lewis GS, Bryce CD, Davison AC, Hollenbeak CS, Piazza SJ, Armstrong AD., "Location of the optimized centerline of the glenoid vault: a comparison of two operative techniques with use of three-dimensional computer modeling." J Bone Joint Surg Am, 2010;92:1188-94. doi:10-2106/JBJS.I.00131. (8 pages).

Mahfouz M, Nicholson G, Komistek R, Hovis D, Kubo M., "In vivo determination of the dynamics of normal, rotator cuff-deficient, total, and reverse replacement shoulders." J Bone Joint Surg Am. 2005;87 Suppl 2:107-13. doi:10.2106/JBJS.E.00483 (8 pages).

Massimini DF, Li G, Warner JP., "Glenohumeral contact kinematics in patients after total shoulder arthroplasty." J Bone Joint Surg Am. Apr. 2010;92(4):916-26. doi:10.2106/JBJS.H.01610. (12 pages).

Matsen FA., "Early effectiveness of shoulder arthroplasty for patients who have primary glenohumeral degenerative joint disease." J Bone and Joint Surg 1996;78-A:260-4. No doi found. (6 pages).

Nyffeler RW, Sheikh R, Atkinson TS, Jacob HA, Favre P, Gerber C., "Effects of glenoid component version on humeral head displacement and joint reaction forces: an experimental study." J Shoulder Elbow Surg. 2006;15:625-9. doi:10.1016/j.jse.2005.09.016. (5 pages).

Nyffeler RW, Werner CM, Sukthankar A, Schmid MR, Gerber C., "Association of a large extension of the acromion with rotator cuff tears." J. Bone Joint Surg Am. 2006;88-800-5. No doi found (10 pages).

Pappas GP, Blemker SS, Beaulieu CF, McAdams TR, Whalen ST, Gold GE., "In vivo anatomy of the Neer and Hawkins sign positions for shoulder impingement." J Shoulder Elbow Surg 2006;15:40-9. doi:10.1016/j.jse.2005.04.007. (10 pages).

Pearl ML, Krurtz S., "Geometric analysis of commonly used prosthetic systems for proximal humeral replacement." J Bone Joint Surg 1999;81-A:660-71. No doi found (13 pages).

Scalise JJ, Codsi MJ, Bryan J, Brems JJ, Iannotti JP., "The influence of three-dimensional computed tomography images of the shoulder

(56) References Cited

OTHER PUBLICATIONS in preoperative planning for total shoulder arthroplasty." J Bone Joint Surg Am. 2008;90:2438-45.doi:10.2106/JBJS.G.01341. (9 pages).

Schiffern SC, Rozencwaig R, Antoniou J, Richardson ML, Matsen FA III., "Anteroposterior centering of the humeral head on the glenoid in vivo." Am J Sports Med. 2002;30(3):382-7. No doi found. (7 pages).

Soslowsky LJ, Flatow EL, Bigliani LU, Pawluk RJ, Ateshian GA, Mow VC., "Quantitation of in situ contact areas at the glenohumeral joint: a biomechanical study." J Orthop Res. 1992;10:524-34. doi:10.1002/jor.1100100407. (11 pages).

Takase K, Yamamoto K, Imakiire A, Burkhead WZ Jr., "The radiographic study in the relationship of the glenohumeral joint." J Orthop Res. 2004;22:298-305. doi:10.1016/S0736-0266(03)00187-6 (8 pages).

Tokgoz N, Kanatli U, Voyvoda NK, Gultekin S, Bolukbasi S, Tali ET., "The relationship of glenoid and humeral version with supraspinatus tendon tears." Skeletal Radion. 2007;36:509-14. No doi found. (6 pages).

Werner CML, Weishaupt D, Blumenthal S, Curt A, Favre P, Gerber C., "Effect of experimental suprascapular nerve block on active glenohumeral translations in vivo." J Orthop Res 2006;24:491-500. doi:10.1002/jor.20011. (10 pages).

Wirth MA, Rockwood CA., "Current concepts review—complications of total shoulder replacement arthroplasty." J Bone Joint Surg Am 1996; 78-A; 603-616. No doi found. (15 pages).

Antuna et al., "Glenoid revision surgery after total shoulder arthroplasty," Journal of Shoulder Elbow Surgery, 2001, pp. 217-224, vol. 10, Rochester, MN (8 pages).

Boileau P, Walch G., "The three dimensional geometry of the proximal humerus. Implications for the surgical technique and prosthetic design." J. Bone Joint Surg Br 1997;79-B:857-65. doi:10.1302/0301-620X.79B5.7579 (9 pages).

Boyer PJ, Massimini DF, Gill TJ, Papannagari R, Stewart SL, Warner JP, Li G., "In vivo articular cartilage contact at the glenohumeral joint: preliminary report." J. Orthop Sci. 2008;13:359-65.doi:10.1007/s00776-008-1237-3 (7 pages).

Bryce CD, Davison AC, Lewis GS, Wang, Flemming DJ, Armstrong AD., "Two dimensional glenoid version measurements vary with coronal and sagittal scapular rotation." J Bone Joint Surg Am. 2010;92-692-9.doi.10.2106/JBJS.I.00177 (8 pages).

Codsi et al., "Normal glenoid vault anatomy and validation of a novel glenoid implant shape," Journal of Shoulder Elbow Surgery, May/Jun. 2008, pp. 471-478, vol. 17, Austria (8 pages).

Couteau B, Mansat, Darmana R, Mansat M., Egan J., "Morphological and mechanical analysis of the glenoid by 3D geometric reconstruction using computed tomography." Clin Biomech 2000;15(suppl1):8-12.doi:10.1016/S0268-0033 (00)00052-8 (5 pages).

Couteau B, Mansat P. Estivales E, Darmana R. Mansat M., Egan J., "Finite element analysis of the mechanical behavior of a scapula implanted with a glenoid prosthesis." Clin Biomech 2001;16:566-75. doi:10.1016/S0268-0033(01) 00029-8 (10 pages).

Couteau B, Mansat P, Mansat M, Darmana R, Egan J., "In vivo characterization of glenoid with use of computed tomography." J Shoulder Elbow Surg 2001;116-22 (7 pages).

De Wilde LF, Verstraeten T, Speeckaert W, Karelse A., "Reliability of the glenoid plane." J Shoulder Elbow Surg. 2010;19:414-22. doi:10.1016/j.jse.2009.10.005. (9 pages).

Graichen H, Hinterwimmer S, von Eisenhart-Rothe R, Vogl T. Englmeier KH, Eckstein F., "Effect of abducting and adducting muscle acitivity on glenohumeral translation, scapular kinematics and subacromial space width in vivo." Journal of Biomechanics 2005;38:755-60. doi:10.1016/j.jbiomech.2004.05.020. (6 pages).

Graichen H, Stammberger T. Bonel H, Karl-Hans E, Reiser M, Eckstein F., "Glenohumeral translation during active and passive elevation of the shoulder—a 3D open-MRI study." Journal of Biomechanics 2000;33:609-13.doi:10.1016/S0021-9290(99)00209-2. (5 pages).

Harryman DT, Sidles JA, Harris SL, Lippitt SB, Matsen FA., "The effect of articular conformity and the size of the humeral head component on laxity and motion after glenohumeral arthroplasty." J. Bone Joint Surg Am 1995;77-A:555-63.No doi found. (10 pages).

Huysmans PE, Haen PS, Kidd M, Dhert WJ, Willems JW., "The shape of the inferior part of the glenoid: a cadaveric study." J Shoulder Elbow Surg. 15(6):759-63. doi:10.1016/j.jse.2005.09.001 (5 pages).

Karelse et al., "The Pillars of the Scapula", Clinical Anatomy, 2007, pp. 392-399, vol. 20, Belgium (8 pages).

Matsen, Frederick, et al., "Shoulder Arthroplasty: The Socket Perspective," J Shoulder Elbow Surg., 2007, 16:241S-247S (7 pages).

* cited by examiner

CIRCULAR GLENOID METHOD FOR SHOULDER ARTHROPLASTY

CROSS-REFERENCE TO RELATED APPLICATIONS

This application is related to U.S. patent application Ser. No. 13/051,026, entitled "Combination Reamer/Drill Bit for Shoulder Arthroscopy", which was filed on Mar. 18, 2011, U.S. patent application Ser. No. 13/051,041, entitled "Device and Method for Retroversion Correction for Shoulder Arthroscopy", which was also filed on Mar. 18, 2011, and U.S. patent application Ser. No. 13/051,062, entitled "Revision Glenoid Device and Method", which was also filed on Mar. 18, 2011 (now U.S. Pat. No. 8,551,177 issued Oct. 8, 2013), the disclosures of which are hereby totally incorporated by reference in their entirety.

TECHNICAL FIELD OF THE INVENTION

The present invention relates generally to the field of orthopedics, and, more particularly, to glenoid component apparatuses for shoulder arthroplasty and methods for using them.

BACKGROUND

Figure 1:
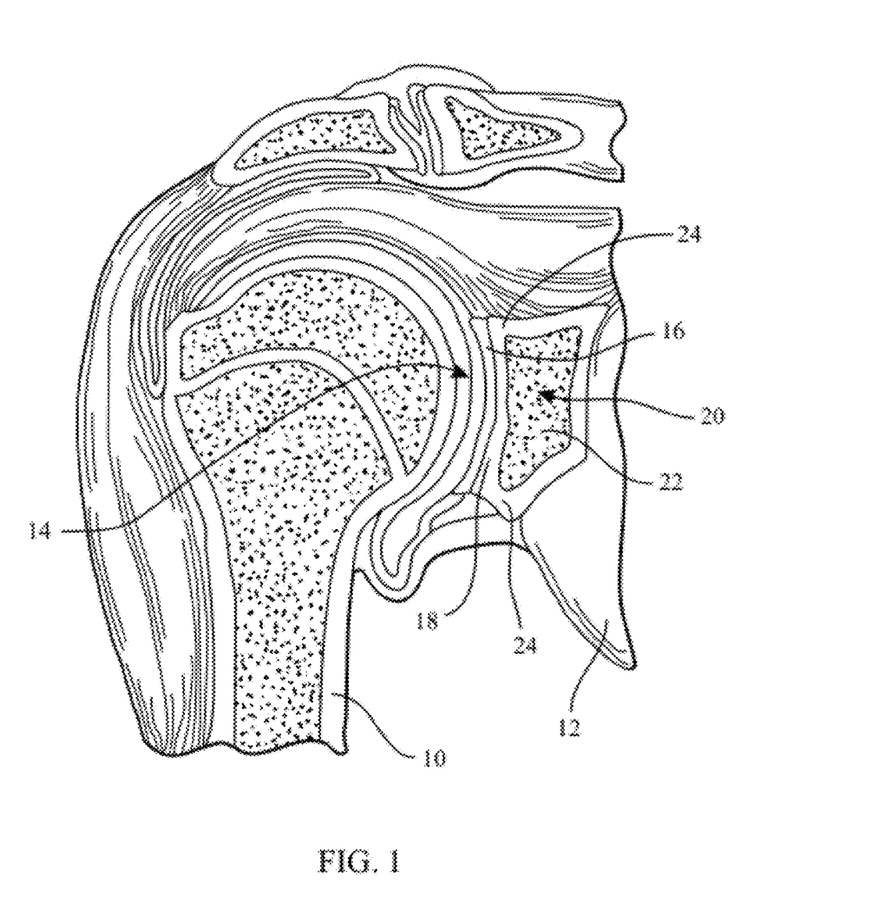
FIG. 1 depicts a coronal view of an anatomically normal shoulder joint.

As depicted in FIG. 1, a typical shoulder or glenohumeral joint is formed in a human body where the humerus 10 movably contacts the scapula 12. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa 14 and suitably resecting cancellous bone 22 from the glenoid vault 20.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical and positioning of the humeral component is accomplished by using the anatomical neck of the humerus as the reference plane for reconstruction of the humeral head.

Traditionally, shoulder joints have been understood to exhibit translation of the humeral component on the glenoid component in addition to rotation. Thus, the articulating surface of the glenoid is typically formed with a radius of curvature that is much larger than the radius of curvature of the humeral component. The increased radius of curvature of the glenoid articulating surface can be from 2-6 mm larger than the radius of curvature for the humeral component in these systems.

Figure 2:
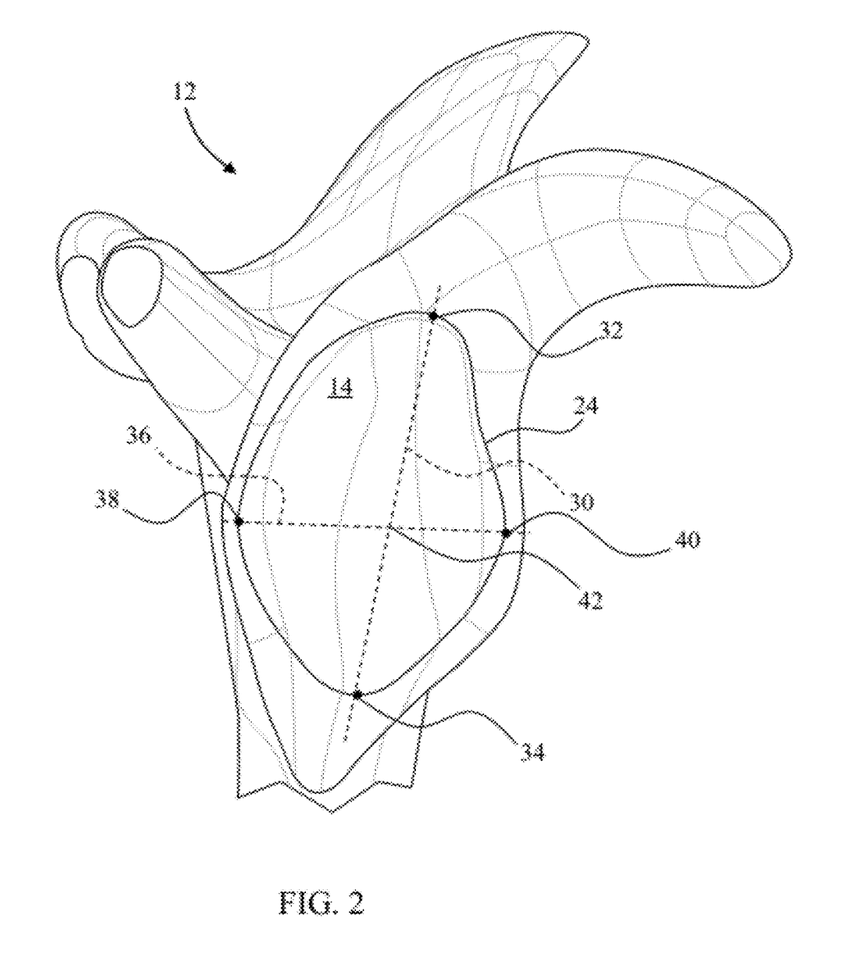
FIG. 2 depicts a sagittal view of the shoulder joint of FIG. 1.

In known systems, the glenoid component is positioned in the geometric center of the glenoid fossa. The geometric center is established by generating a line from the most superior point of the glenoid rim to the most inferior point of the glenoid rim ("Saller's line"). A second line is generated between the most posterior point of the glenoid rim and the most anterior point of the glenoid rim. The intersection of the two generated lines is considered to be the geometric center of the area circumscribed by the glenoid rim. By way of example, FIG. 2 depicts a sagittal view of the scapula 12. In FIG. 2, Saller's line 30 extends between the most superior point 32 of the glenoid rim 24 to the most inferior point 34 of the glenoid rim 24. A second line 36 extends from the most posterior point 38 of the glenoid rim 24 and the most anterior point 40 of the glenoid rim. The geometric center 42 of the glenoid fossa 14 is located at the intersection of the line 36 and Saller's line 30. As used herein, the terms anterior, posterior, superior, and inferior, unless otherwise specifically described, are used with respect to the orientation of the scapula 12 as depicted in FIG. 2.

While known systems achieve varying degrees of success in replicating normal kinematics, the systems are susceptible to various modes of failure. One mode of failure is known as the "rocking horse" effect. In this failure mode, high shear forces on the glenoid component are experienced as the humeral component translates to the edges of the glenoid component. The unbalanced loading of the glenoid component results in loosening of the component.

There remains a need for a glenoid component that allows for establishing normal kinematics. There is a further need for a technique that facilitates positioning of such a component. A glenoid component that can be positioned in a manner that reduces the potential for rocking horse failure of the component is also needed.

SUMMARY OF THE INVENTION

The present invention in one embodiment provides a method of shoulder arthroplasty including accessing a scapula, identifying an inferior glenoid circle center of the scapula, preparing a glenoid fossa of the scapula to receive a prosthesis, selecting a glenoid component, and implanting the selected glenoid component based upon the identified inferior glenoid circle center in the prepared glenoid fossa.

In an alternative embodiment, a method of implanting a glenoid component includes obtaining an image of a scapula, identifying an inferior glenoid circle center of the scapula based upon the image, selecting a glenoid component, preparing a glenoid fossa of the scapula to receive a prosthesis, and implanting the selected glenoid component in the prepared glenoid fossa based upon the identified inferior glenoid circle center.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

DETAILED DESCRIPTION

Like reference numerals refer to like parts throughout the following description and the accompanying drawings.

Figures 3, 4, 5:
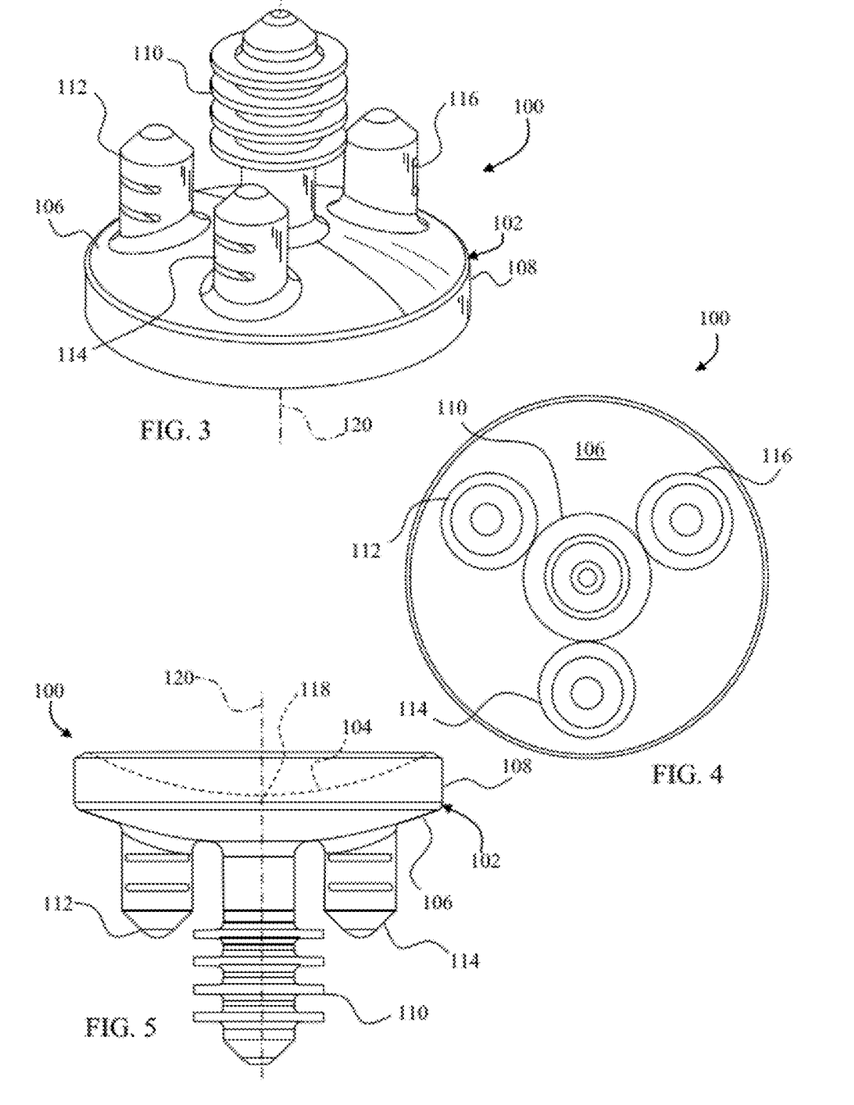
FIG. 3 depicts a bottom perspective view of a circular glenoid component that may be implanted in a scapula in accordance with principles of the invention.
FIG. 4 depicts a bottom plan view of the circular glenoid component of FIG. 3.
FIG. 5 depicts a side plan view of the circular glenoid component of FIG. 3.

FIGS. 3-5 depict a glenoid component 100. The glenoid component 100 includes a body portion 102 including a spherical articulating surface 104 and an opposite bone contacting surface 106. An outer wall 108 extends away from the bone contacting surface 106 and defines an outer periphery of the body portion 102. The bone contacting surface 106 is generally convex. A finned center peg 110 extends away from the nadir of the bone contacting surface 106 as viewed in FIG. 5. Three offset pegs 112, 114, and 116 extend away from the bone contacting surface 106 at locations between the center peg 110 and the outer wall 108. The nadir 118 of the spherical articulating surface 104 is located on the centerline 120 of the glenoid component 100.

The glenoid component 100 in this embodiment is an integrally formed unit made from a durable biocompatible plastic or any other suitable durable biocompatible material. For example, the glenoid component 100 may be made from a polyethylene. One particular polyethylene that is well suited for glenoid component 100 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference.

In embodiments wherein the articulating surface 104 and the other portions of the glenoid component 100 are made from different materials, the portions of the glenoid component 100 other than the articulating surface 104 may be made from a suitable biocompatible metal such as, for example, a cobalt chromium alloy, a stainless steel alloy, a titanium alloy, or any other suitable durable material. In these embodiments, the articulating surface 104 is secured to the body portion 102 in any suitable manner. For example, articulating surface 104 may be bonded to body portion 102, or articulating surface 104 could be made from polyethylene and compression molded to body portion 102. Alternately, the articulating surface 104 may be glued to the body portion 102 by, for example, an adhesive. Alternatively, articulating surface 104 may be mechanically interlocked to the body portion 102 by taper locking or otherwise press-fitting the articulating surface 104 into the body 102 and the body 102 may include any other suitable interlocking features, for example, rib(s), lip(s), detent(s), and/or other protrusion(s) and mating groove(s), channel(s), or indent(s) (not shown).

In alternative embodiments, one or more of the outer wall 108, the bone contacting surface 106, the center peg 110 and the offset pegs 112, 114, and 116 may include a porous coating to facilitate bone in-growth into the glenoid component 100. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference.

Figure 6:
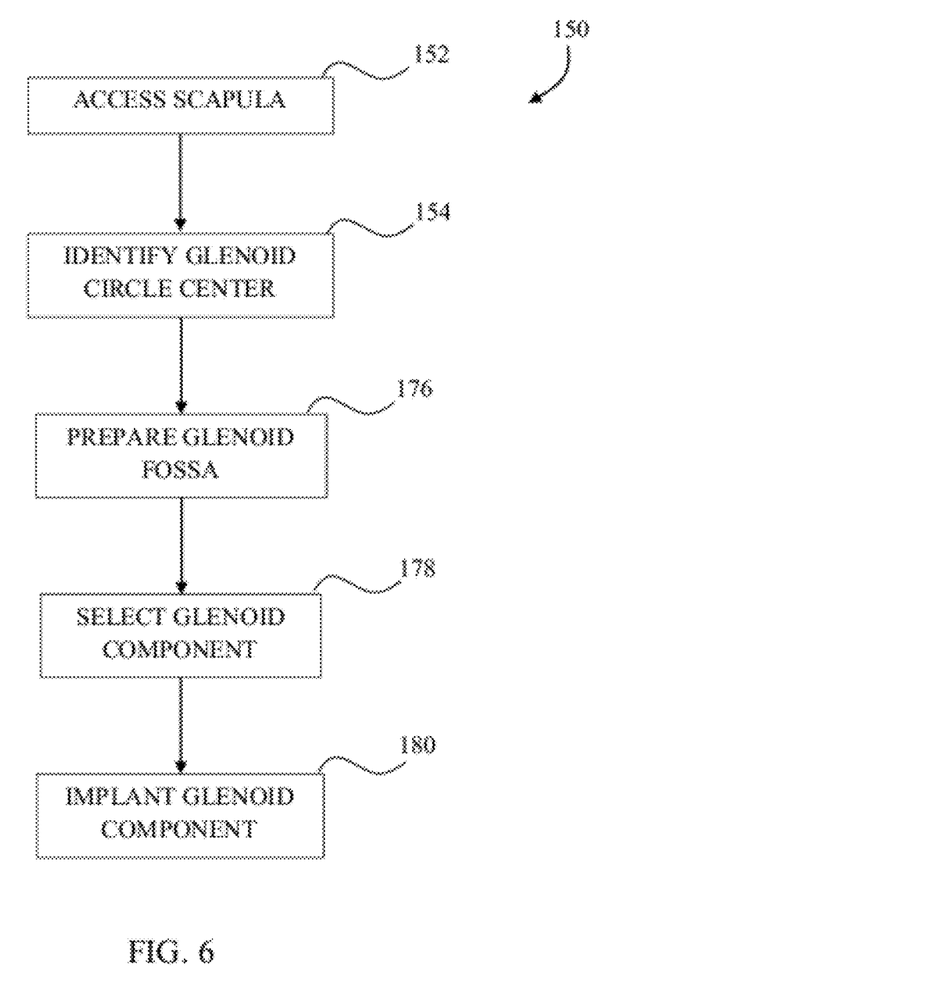
FIG. 6 depicts a medical procedure that may be used to implant the circular glenoid component of FIG. 3 into a scapula based upon identifying an inferior glenoid circle center of the scapula.

The glenoid component 100 may be implanted into the scapula 12 in accordance with a procedure 150 depicted in FIG. 6. In accordance with the procedure 150, a scapula 12 is accessed at block 152 in accordance with a desired surgical approach. At block 154, the center of an inferior glenoid circle, further described below, is identified for the scapula. While visual identification of the inferior glenoid circle and hence the center of the inferior glenoid circle is possible once the scapula 12 is accessed at block 152, the center of the inferior glenoid circle may alternatively be identified prior to or after incising a patient with the aid of imaging or other techniques.

By way of example, a CT scanner such as a Somatom Volume Zoom commercially available from Siemens Medical Solutions USA, Inc. of Malvern, Pa. may be used. The CT scanner may be set for matrix: 512/Kv: 140/eff. mAs: 350. The scan field of view (SFOV) may be set for 500, with the field of view (FOV) adapted to the individual patient, maximally 500 for both shoulders and minimally 150 for one shoulder. To obtain the desired images, the patient is then positioned in the CT-scanner tunnel in a dorsal recumbency, with a cushion on the belly and a strap around the body and the cushion to keep the arm adducted in the coronal plane and the forearm flexed in the sagittal plane of the body. The glenohumeral joint may then be scanned with 1.5 mm slices.

In order to facilitate analysis of the images obtained from the CT scanner, the images may be imported into a medical imaging computer software such as Mimics® 11.02 for Intel X86 Platform V11.2.2.11992-2007 commercially available from Materialise Inc., Haasrode Belgium. The imported images may be used to create three dimensional images of the shoulder which allow the bones of the joint to be digitally separated and different views of the bones may be obtained.

Figure 7:
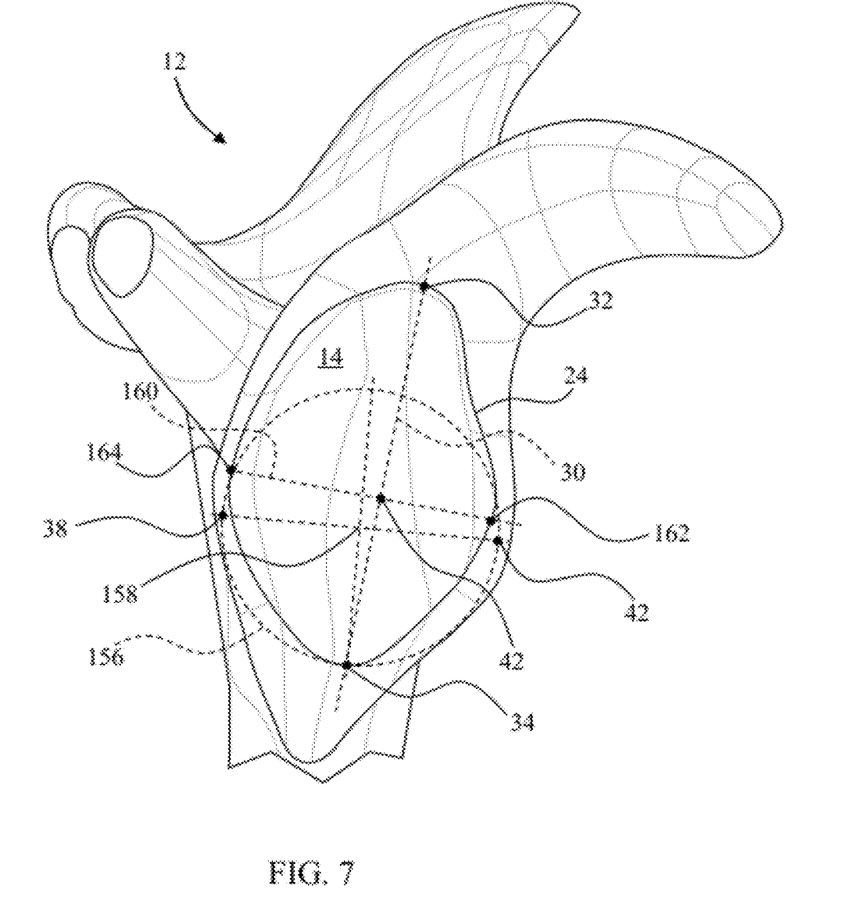
FIG. 7 depicts the sagittal view of the shoulder joint of FIG. 2 with different coordinate systems defined thereon.

Once a sagittal view of the scapula 12 is obtained in the foregoing fashion, the inferior point 34, the posterior point 38, and the anterior point 40 may be identified (see FIG. 2). Then, a best fit circle defined by the inferior point 34, the posterior point 38, and the anterior point 40 is identified. The best fit circle is the inferior glenoid circle, such as inferior glenoid circle 156 depicted in FIG. 7. Once the best fit inferior glenoid circle 156 is identified, the center 158 of the inferior glenoid circle 156 is defined. As shown in FIG. 7, the center 158 of the inferior glenoid circle 156 is located inferiorly and posteriorly to the geometric center 42.

Identification of the inferior glenoid circle center 158 at block 154 is performed in order to better position a glenoid component 100 as compared to traditional points of reference such as the geometric center 42. Specifically, while known prosthetic systems are designed to allow for translation of the humeral component with respect to the glenoid component, the inventors hypothesize that in normal kinematics of the shoulder joint the humerus 10 does not exhibit translation along the glenoid fossa 14. Rather, such observed translation indicates that normal kinematics have not been achieved. If a normal shoulder does not exhibit translation, then restoration of normal kinematics would entail configuring and positioning a glenoid component such that an unloaded humeral component would simply spin on the glenoid component.

The location at which the humeral component would spin on the glenoid component, the "spinning point" would thus be defined as a point in a plane defined by the glenoid fossa 14 at which a line from the origin (R) of the humeral component, which is assumed to be spherical, to the defined plane is orthogonal to the defined plane. Proof of the usefulness in identifying the inferior glenoid circle center 158 in locating the spinning point of a shoulder joint was obtained by analysis of Ct scans of 152 shoulders using the CT scanner and parameters described above.

Once the scans of the 152 shoulders were obtained and imported into the medical imaging computer software described above, two different Cartesian coordinate systems were defined to assess the usefulness of identifying the inferior glenoid circle in determining the location of the spinning point of a shoulder joint. Both systems were based upon a plane defined by the inferior point 34, the posterior point 38, and the anterior point 40. This plane was selected for consideration since the plane defined by those points has been proven to exhibit the least variation between individuals as compared to planes defined by other reference points on the scapula. The two systems are described with reference to FIG. 7 and FIG. 2.

In one system, defined as a linear-point system, an origin is defined as the intersection of the line 36 and Saller's line 30 on a plane defined by the inferior point 34, the posterior point 38, and the anterior point 40. The origin of the linear-point coordinate system is thus the geometric center 42 (see FIG. 2). The Y-axis in this system is defined as a line extending between the geometric center 42 and the inferior point 34. The Y-axis is thus Saller's line 30. The X-axis 160 in this system is defined as a line perpendicular to the Y-axis (Saller's line 30) which includes the geometric center 42, as well as including an anterior point 162 and posterior point 164 both of which are located on the glenoid rim 24. The Z-axis is defined as a line perpendicular to the defined plane and including the origin, geometric center 42.

A circular coordinate system was also defined. In the circular system, the origin is defined as the inferior glenoid circle center 158. The Y-axis 164 in this system is defined as a line including the inferior glenoid circle center 158 and the inferior point 34. The X-axis 166 in this system is defined as a line perpendicular to the Y-axis 164 which includes the inferior glenoid circle center 158, as well as including an anterior point 168 and posterior point 170 both of which are located on the glenoid rim 24. The Z-axis is defined as a line perpendicular to the defined plane and including the origin, inferior glenoid circle center 158.

In analyzing the obtained scans, the humeral articulating surface is assumed to be a spherical surface with an origin (R). Thus, for each reference system the "spinning point" is defined to be the location on the defined plane at which a line directly between the R and the plane forms a ninety degree angle. In both of the above defined coordinate systems, a projection superior to the respective X-axis is defined to be greater than 90 degrees and a projection posterior to the respective Y-axis is defined to be greater than 90 degrees.

Using the above described circular coordinate system, the obtained images were analyzed to quantify any offset between the spinning point and the inferior glenoid circle center 158. Analysis was also performed using the linear-point coordinate system to quantify any offset between the spinning point and the geometric center 42 since the geometric center 42 is a commonly used reference point for positioning of a glenoid component.

Quantification of the offset between the spinning point and the geometric center was obtained by measuring the length of the line between the R and the geometric center 42 and determining the angulation of that line based upon the above described linear point coordinate system for each of the shoulders (the "intersecting-point measurement"). Quantification of the offset between the spinning point and the inferior glenoid circle center 158 was obtained by measuring the length of the line between the R and the inferior glenoid circle center 158 and determining the angulation of that line based upon the above described circular coordinate system for each of the shoulders (the "circular measurement").

The results of the foregoing measurements were statistically analyzed using one-sample t-tests, by hypothesizing that the mean angle did not deviate from 90 degrees. Means and variances of angles and distances were compared between the intersecting-point measurements and the circular measurements using paired two-sample t-tests and modified Levene tests. Paired t-tests were also used to compare corresponding distances within each of the measurement techniques. Mixed model analysis was applied to the results to adjust for age, sex, and side of the subjects. For continuous, normally distributed outcome measures, intra- and inter-observer reliability was assessed by intra-class correlation coefficients (ICC) based upon two-way random effect models using an absolute agreement definition. All statistical analyses were performed using IBM SPSS statistics, version 18, commercially available form SPSS, Inc. of Chicago, Ill.

Using three independent reviewers, the mean length of the longitudinal or craniocaudal axis (between the inferior point 34 and the superior point 32) was 35 mm (95% Cl 34.87 mm-35.83 mm). The mean length of the anteroposterior axis (between the posterior point 38 and the anterior point 40) was 27.02 mm (95% Cl 26.55 mm-27.5 mm). The mean diameter of the inferior glenoid circle 156 was 25.87 mm (95% Cl 25.45 mm-26.30 mm).

Based upon the intersecting-point measurement, the actual spinning point when projected onto the defined plane was located inferiorly to the craniocaudal axis (89.11 degrees, 95% Cl 88.38°-89.86°) and posteriorly to the anteroposterior axis (95.30 degrees, 95% Cl 94.48°-96.13°). The length of the line between the geometric center 42 and R was 24.77 mm (95% Cl 24.41 mm-25.13 mm).

Based upon the circular measurement, the actual spinning point when projected onto the defined plane was located superiorly to the craniocaudal axis (91.86 degrees, 95% Cl 91.35°-93.37°) and posteriorly to the anteroposterior axis (91.86 degrees, 95% Cl 91.17°-92.46°). The length of the line between the center 158 of the inferior glenoid circle 156 and R was 24.72 mm (95% Cl 24.35 mm-25.08 mm).

In obtaining the foregoing results, the intra- and inter-observer variability was considered very good to acceptable. Reliability was assessed using inter- and intra-observer concordance, expressed as interclass correlation coefficients.

Consequently, identifying the inferior glenoid circle center 158 of the inferior glenoid circle 156 for a particular patient provides a good estimation of the location of the spinning point for the patient since the line between the inferior glenoid circle center 158 and the origin of the humeral component is nearly perpendicular to the defined plane. If desired, an offset slightly superior and posterior to the center 158 may be incorporated to attempt to more accurately define the spinning point.

Returning to the procedure 150 of FIG. 6, once the center of the inferior glenoid circle is identified at block 154, the glenoid fossa 14 is prepared to receive the selected glenoid component 100 at block 176. Preparation of the glenoid fossa 14 may include planarization of the glenoid fossa 14, and drilling holes to receive a particular glenoid component, such as the center peg 110, and the offset pegs 112, 114, and 116. Preparation of the glenoid fossa 14 may be computer assisted, including the use of computer aided procedures to position a guide wire in the glenoid fossa 14 based upon the identified inferior glenoid circle center 158. If desired, the guide wire may be positioned on the glenoid fossa 14 at a location slightly offset from the inferior glenoid circle center 158 in a posterior and superior direction.

Once the glenoid fossa 14 is prepared, a glenoid component 100 is selected at block 178. In one embodiment, a circular glenoid component 100 sized to fit within the area circumscribed by both the glenoid rim 24 and the inferior glenoid circle 156 with the nadir 118 at or slightly posterior and superior to the center 158 of the inferior glenoid circle 156 is selected. Selection of the glenoid component 100 may be based upon a variety of other factors. Such factors include the availability of bony structures which can be used to anchor the glenoid component 100. Accordingly, in a kit including a number of different glenoid components 100, a variety of differently sized glenoid components 100 may be provided along with a variety of peg configurations. The kit may further include glenoid components 100 that do not include any pegs. Some of the glenoid components 100 which do not include pegs may be configured for use with bone screws.

Figure 8:
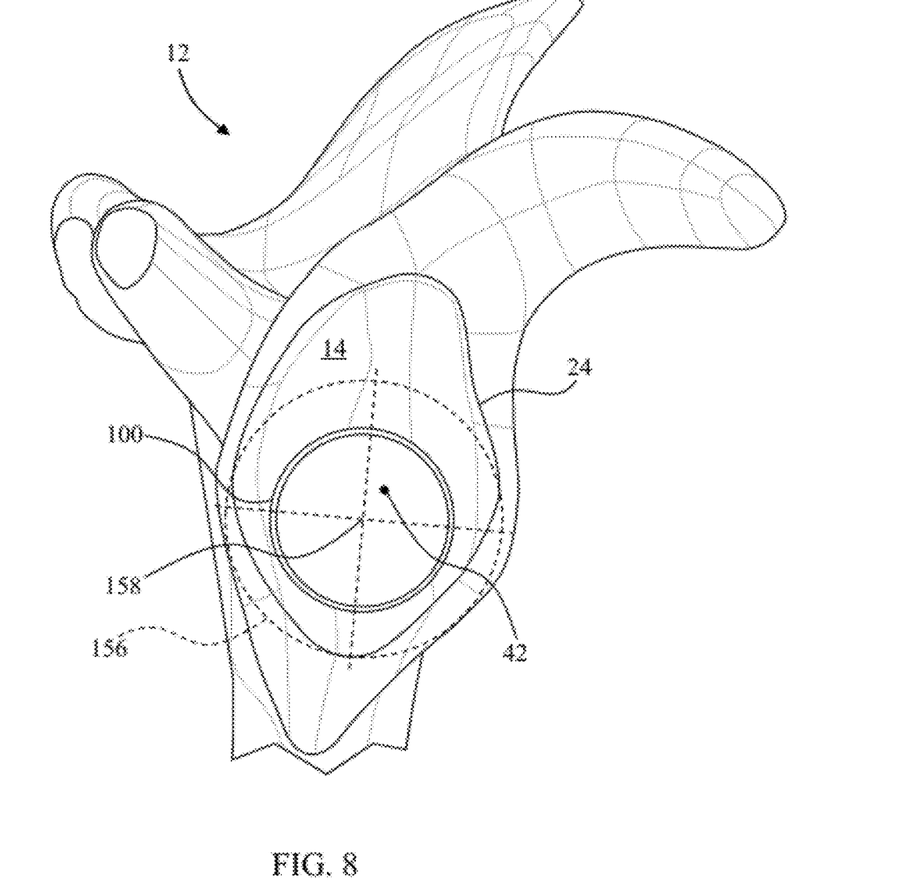
FIG. 8 depicts the circular glenoid component of FIGS. 3-5 implanted into the scapula of FIG. 1.

After the glenoid fossa 14 is prepared, and the glenoid component is selected, then, at block 180, the selected glenoid component 100 is implanted in the prepared glenoid fossa 14 resulting in the configuration depicted in FIG. 8.

The procedure 150 may be modified in a number of ways. By way of example, while in the above example the glenoid component 100 was implanted with the nadir 118 aligned with the inferior glenoid circle center 158 at block 180, the nadir 118 may alternatively be offset from the inferior glenoid circle center 158. For example, the analysis described above indicated that a line from the origin R of the humeral component that is perpendicular to the plane defined by the inferior point 34, the posterior point 38, and the anterior point 40 (see FIG. 2) is typically offset from the inferior glenoid circle center by about 1.1 mm in a direction superiorly and posteriorly from the inferior glenoid circle center 158. Accordingly, the nadir 118 may be positioned based upon location of the inferior glenoid circle center 158 at a location about 1.1 mm superiorly and posteriorly from the inferior glenoid circle center 158. Imaging and computer based systems may be used to assist in the positioning of the glenoid component at this location.

Alternatively, the spinning point of a particular shoulder may be identified such as by use of a CT scanner as described above. In this embodiment, identification of the inferior glenoid circle center 158 and quantification of the offset of the inferior glenoid circle center 158 from the spinning point of the shoulder may occur prior to surgically accessing the shoulder. Then, the glenoid component 100 may be implanted such that the nadir 118 is aligned with the determined spinning point.

Moreover, while a specific sequence was described in the procedure 150, many of the steps may be performed in a different order and/or simultaneously with other of the steps. For example, in certain instances, the specific anatomy will dictate the manner in which the glenoid fossa can be prepared, which will in turn dictate or influence the glenoid component that may be selected. In other instances, the anatomy may allow for different types of glenoid components to be used. In such instances, the selected glenoid component may influence the manner in which the glenoid fossa is prepared to receive the selected glenoid component.

In accordance with the methods described above, a glenoid component with a spherical articulating surface is implanted at or very near to the spinning point of a shoulder. Because of the location of the glenoid component, a humeral component with a radius of curvature matched to the radius of curvature of the articulating surface may be used to provide a constrained fit. As used herein, the term "matched" means a difference in the radii of curvature of the articulating surfaces of less than 2 mm.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method of implanting a glenoid component having a concave articulating surface comprising:
   accessing a scapula;
   identifying an inferior glenoid circle center of the scapula by identifying an inferior point of a glenoid rim, identifying an anterior point of the glenoid rim, identifying a posterior point of the glenoid rim, and establishing a best fit circle based upon the identified inferior point, the identified anterior point, and the identified posterior point;
   preparing a glenoid fossa of the scapula to receive the glenoid component;
   selecting the glenoid component having the concave articulating surface; and
   implanting the selected glenoid component based upon the identified inferior glenoid circle center in the prepared glenoid fossa.

2. The method of claim 1, wherein selecting comprises:
   selecting the glenoid component with a circular outer periphery.

3. The method of claim 2, wherein the glenoid component includes a spherical articulating surface, the method further comprising:
   aligning a nadir of the spherical articulating surface with the glenoid fossa based upon the identified inferior glenoid circle center.

4. The method of claim 3, wherein implanting the selected glenoid component comprises:
   implanting the selected glenoid component with the nadir aligned with the identified inferior glenoid circle center.

5. The method of claim 3, wherein implanting the selected glenoid component comprises:
   implanting the selected glenoid component with the nadir offset from the identified inferior glenoid circle center.

6. The method of claim 5, wherein implanting the selected glenoid component comprises:
   implanting the selected glenoid component with the nadir offset superiorly and posteriorly from the identified inferior glenoid circle center.

7. The method of claim 1, wherein identifying the inferior glenoid circle center comprises:
   obtaining an image of the scapula; and using the obtained image to identify the inferior glenoid circle center.

8. The method of claim 7, further comprising:
positioning a guide on the scapula based upon the obtained image.

9. The method of claim 8, wherein positioning the guide comprises:
positioning the guide at the identified inferior glenoid circle center.

10. The method of claim 8, wherein positioning the guide comprises:
positioning the guide at a location posterior and superior to the identified inferior glenoid circle center.

11. The method of claim 10, wherein:
identifying the inferior point of the glenoid rim comprises identifying the most inferior point of the glenoid rim;
identifying the anterior point of the glenoid rim comprises identifying the most anterior point of the glenoid rim;
identifying the posterior point of the glenoid rim comprises identifying the most posterior point of the glenoid rim; and
establishing the best fit circle comprises establishing a bets fit circle based upon the identified most inferior point, the identified most anterior point, and the identified most posterior point.

12. The method of claim 1, wherein:
identifying the inferior point of the glenoid rim comprises identifying the most inferior point of the glenoid rim;
identifying the anterior point of the glenoid rim comprises identifying the most anterior point of the glenoid rim;
identifying the posterior point of the glenoid rim comprises identifying the most posterior point of the glenoid rim; and
establishing the best fit circle comprises establishing a bets fit circle based upon the identified most inferior point, the identified most anterior point, and the identified most posterior point.

13. A method of implanting a glenoid component having a concave articulating surface comprising:
obtaining an image of a scapula;
identifying an inferior glenoid circle center of the scapula based upon the image by identifying an inferior point of a glenoid rim, identifying an anterior point of the glenoid rim, identifying a posterior point of the glenoid rim, and establishing a best fit circle based upon the identified inferior point, the identified anterior point, and the identified posterior point;
selecting the glenoid component having the concave articulating surface;
preparing a glenoid fossa of the scapula to receive a prosthesis; and
implanting the selected glenoid component in the prepared glenoid fossa based upon the identified inferior glenoid circle center.

14. The method of claim 13, wherein selecting comprises:
selecting the glenoid component with a circular outer periphery.

15. The method of claim 13, wherein the glenoid component includes a spherical articulating surface, the method further comprising:
aligning a nadir of the spherical articulating surface with the glenoid fossa based upon the identified inferior glenoid circle center.

16. The method of claim 15, wherein implanting the selected glenoid component comprises:
implanting the selected glenoid component with the nadir aligned with the identified inferior glenoid circle center.

17. The method of claim 15, wherein implanting the selected glenoid component comprises:
implanting the selected glenoid component with the nadir offset from the identified inferior glenoid circle center.

18. The method of claim 17, wherein implanting the selected glenoid component comprises:
implanting the selected glenoid component with the nadir offset superiorly and posteriorly from the identified inferior glenoid circle center.

19. The method of claim 17, further comprising:
identifying a spinning point of the scapula; and
determining an offset of the spinning point from the identified inferior glenoid circle center, wherein implanting the selected glenoid component comprises:
implanting the selected glenoid component with the nadir offset from the identified inferior glenoid circle center by the determined offset.

20. The method of claim 19, further comprising:
positioning a guide on the scapula based upon the obtained image.

* * * * *